United States Patent [19]

Fishman et al.

[11] Patent Number: 5,120,724
[45] Date of Patent: Jun. 9, 1992

[54] ALDOSTERONE BIOSYNTHESIS INHIBITOR

[75] Inventors: Jack Fishman, Miami; Elliot Hahn, North Miami Beach; Gregory A. Smith, North Miami, all of Fla.

[73] Assignee: Baker Cummins Pharmaceuticals, Inc., Miami, Fla.

[21] Appl. No.: 775,567

[22] Filed: Oct. 15, 1991

[51] Int. Cl.⁵ .......................... A61K 31/56; C07J 5/00
[52] U.S. Cl. .................................. 514/177; 552/601; 552/544; 552/552; 552/554; 552/555
[58] Field of Search ............... 552/601, 544, 552, 554, 552/555; 514/177

[56] References Cited

U.S. PATENT DOCUMENTS

| | | | |
|---|---|---|---|
| 3,313,698 | 4/1967 | Bertin et al. | 552/544 |
| 3,342,813 | 9/1967 | Sarel et al. | 552/552 |
| 3,483,235 | 12/1969 | Jeger et al. | 552/552 |

Primary Examiner—Marianne M. Cintins
Assistant Examiner—Kimberly J. Kestler
Attorney, Agent, or Firm—Kirschstein, Ottinger, Israel & Schiffmiller

[57] ABSTRACT

Aldosterone biosynthesis inhibitors having substantially no intrinsic antiandrogenic activity are disclosed as well as pharmaceutical compositions containing such compounds and methods of treatment utilizing these compositions.

13 Claims, No Drawings

ALDOSTERONE BIOSYNTHESIS INHIBITOR

BACKGROUND OF THE INVENTION

1. Field of the Invention

The invention relates to inhibitors of aldosterone biosynthesis and compositions and methods for treating hyperaldosteronism.

2. Description of the Prior Art

Primary aldosteronism is the constellation of chemical and clinical abnormalities resulting from the autonomous hypersecretion of the mineralocorticoid aldosterone, as opposed to secondary aldosteronism which refers to hypersecretion of aldosterone in response to a known stimulus such as angiotensin.

Primary aldosteronism is most frequently caused by an aldosterone-secreting adenoma (Conn's syndrome), but it is sometimes associated with adrenal hyperplasia or can be idiopathic in origin.

Hypersecretion of aldosterone, whether primary or secondary, leads to excessive conservation of sodium, causing elevation of blood pressure, suppression of renin production and expansion of extracellular volume. Aldosterone hypersecretion also causes excessive excretion of potassium which may result in, inter alia, hypokalemic alkalosis, muscular weakness, electrocardiographic abnormalities, and impaired renal concentrating capacity. The principal clinical manifestations of primary aldosteronism are hypertension and its sequelae.

The treatment of choice in primary aldosteronism is surgical excision of the adenomatous adrenal gland. However, patients who are poor surgical risks, those who are unwilling to undergo adrenal exploration, and those whose hyperaldosteronism persists after surgery are conventionally treated with an aldosterone antagonist such as spironolactone. Spironolactone promotes natriuresis and inhibits potassium excretion by acting as a competitive antagonist of aldosterone in the cortical collecting duct of the renal tubule. Spironolactone is also commonly administered for several weeks prior to surgery to patients undergoing excision of adrenal adenomas.

While relatively effective in antagonizing the pernicious effects of hyperaldosteronism, spironolactone has marked antiandrogenic side effects, including decreased libido, impotence and gynecomastia in males, and menstrual irregularities in females. These side effects limit the long-term usefulness of the drug, particularly in males. Other untoward effects of spironolactone include diarrhea, rash and urologic disturbances, as well as the development of hyperkalemia in certain patients.

While other potassium-sparing agents (e.g., triamterene and amiloride) have been used to treat the hypertension caused by hyperaldosteronism, such agents are normally not potent when used alone because only a small volume of tubular fluid reaches their distal sites of action in the cortical collecting ducts.

Improved agents for treating hyperaldosteronism and its sequelae are currently being sought.

SUMMARY OF THE INVENTION

It is the object of the present invention to provide a safe and effective pharmaceutical agent for the treatment of hyperaldosteronism and the hypertension and other consequences thereof, which agent does not cause the serious side effects associated with spironolactone. The invention also has as its object providing a method of treatment of hyperaldosteronism and the diseases and symptoms associated therewith. In keeping with these objects and others which will become apparent hereafter, the invention resides in compounds having the following structural formula:

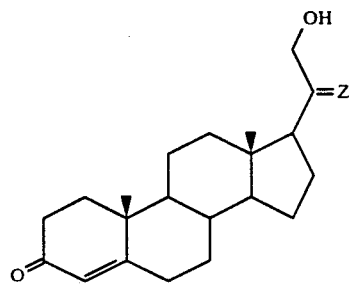

wherein Z is S, $CR_1R_2$ or $NR_5$, and wherein $R_1$ and $R_2$ are each independently selected from the group consisting of hydrogen, halogen, $C_1$-$C_5$ alkyl, $C_1$-$C_5$ alkenyl, aryl, aralkyl, and $-(CH_2)_nYR_3$, $-(CH_2)_nNR_3R_4$ or $-(CH_2)_nCO_2R_3$ wherein n is an integer from 0 to 4, $R_3$ and $R_4$ are $C_1$-$C_4$ alkyl or alkenyl, aryl or aralkyl and Y is oxygen or sulfur, and $R_5$ is selected from the group consisting of $H_2NCONH$, $H_2NCSNH$, $ARH_2N$, $C_1$-$C_5$ alkyl or alkyoxy, aryl and aryloxy. The present invention also comprehends pharmaceutical compositions including compounds of formula I as their active ingredients and methods of treating patients suffering from hyperaldosteronism by administering suitable dosages of such pharmaceutical compositions.

DETAILED DESCRIPTION OF THE INVENTION

Aldosterone is produced endogenously by sequential hydroxylation of the mineralocorticoid desoxycorticosterone (DOC). The primary pathway for aldosterone production is the conversion of DOC to corticosterone by action of the enzyme 11β-hydroxylase, and the subsequent conversion of corticosterone to 18-hydroxycorticosterone and then to aldosterone (which exists in solution as an equilibrium mixture of an aldehyde and a hemiacetal) by sequential action of first and second 18-hydroxylase enzymes. By the secondary pathway for aldosterone production, DOC is first converted to 18-hydroxy-DOC and then 11-hydoxylated to 18-hydroxycorticosterone before being converted by the second 18-hydroxylase enzyme to aldosterone. Both of these pathways are illustrated below:

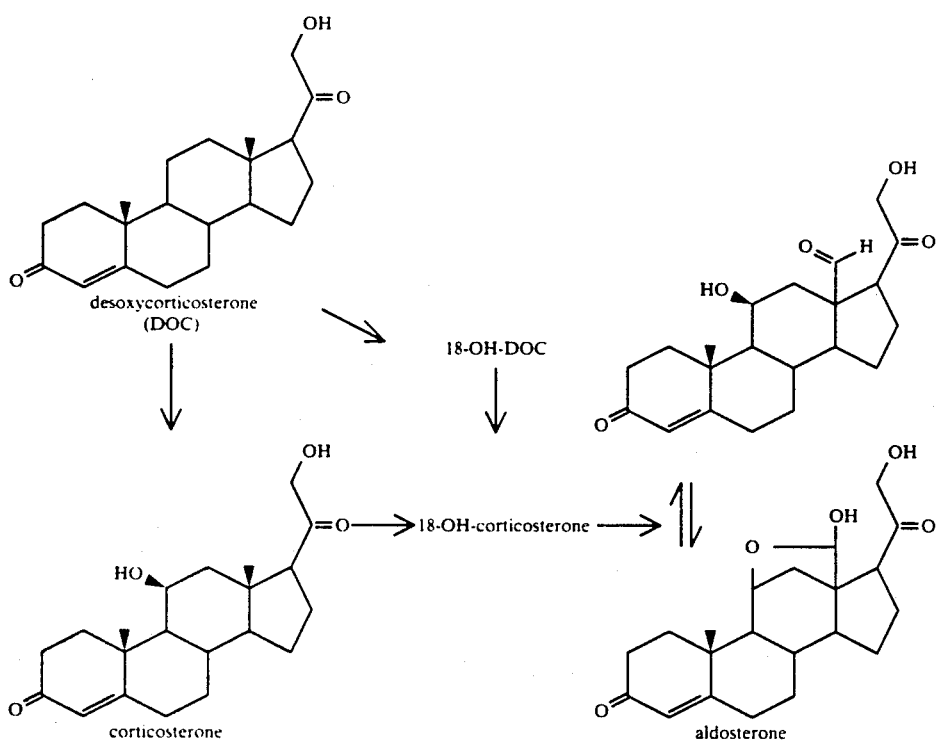

It has been discovered that the novel compounds of formula I block the conversion of 18-hydroxycorticosterone to aldosterone by binding the second 18-hydroxylase enzyme and substantially inhibiting aldosterone biosynthesis. Moreover, it has been found that the novel compounds are substantially devoid of intrinsic antiandrogenic activity, unlike spironolactone which acts as a competitive antagonist not only to aldosterone but also to testosterone. Hence, compounds of formula I do not exhibit the potentially serious antiandrogenic side effects associated with prior art agents used to treat hypersecretion of aldosterone.

By one preferred procedure, the compounds of formula I wherein Z is $CR_1R_2$ may be produced by (a) converting a 21-ester of DOC, for example, DOC acetate, to the corresponding 3-ketal; (b) reduction of the ester to yield DOC-3-ketal; (c) reaction with an appropriate Wittig reagent ($PH_3P=CR_1R_2$) to replace the 20-carbonyl oxygen with $CR_1R_2$, and (d) cleavage of the 3-ketal to restore the 3-carbonyl oxygen.

The compounds of formula I wherein Z is S may be produced by following steps (a) and (b) above to yield DOC-3-ketal, and then proceeding with:

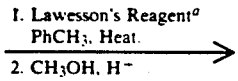

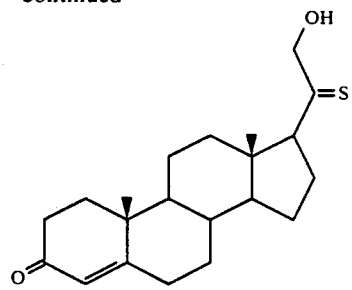

[a]Tet. Lett. 1980, 21, 4061

To produce compounds wherein Z is $NR_5$, the DOC-3-ketal is treated as follows:

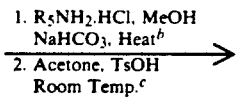

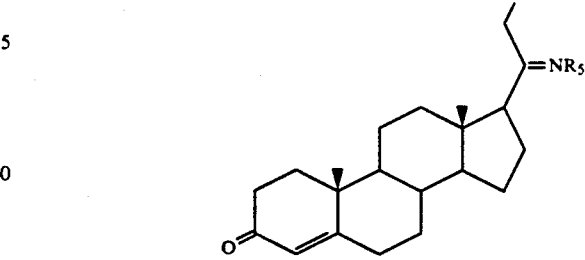

[b]J. Am. Chem. Soc. 1955, 77, 1221.
[c]For selective removal of 3-ketal, Tetrahedron 1959, 5, 15.

The present invention is not, however, limited to any particular process or synthetic route for producing the novel compounds of formula I. It will be readily appreciated by those skilled in the art of synthetic organic chemistry that the novel compounds may be synthesized by a number of different procedures utilizing a variety of reagents.

In accordance with the present invention, the novel aldosterone biosynthesis inhibitors may be administered to patients suffering from hyperaldeosteronism and its sequelae, or patients otherwise suffering from hypertension, hypokalemia or edema associated with sodium retention, in any conventional oral, parenteral, transmucosal, transdermal or other known pharmaceutical dosage form. Oral dosage forms may include conventional tablets, capsules, caplets, pills, lozenges, liquids (solutions, suspensions or elixirs) and the like, including as active ingredients from about 5.0 to about 100 mg of one or more of the compounds of formula I per dosage unit together with inert, pharmaceutically-acceptable excipients, binders, sweeteners, coloring agents and/or other conventional inert additives.

Parenteral dosage forms may include conventional injectable vehicles for the novel compounds, for example, isotonic saline solutions, together with pharmaceutically acceptable buffers and preservatives. The parenteral dosage forms generally contain from about 5 to about 100 mg of the subject aldosterone inhibitors per dosage unit and may be injected by the subcutaneous, intramuscular or intravenous routes.

Suitable transmucosal and transdermal dosage forms may include known sublingual, buccal and intranasal vehicles, as well as patches and topical vehicles containing penetrants which enhance transdermal absorption of the active antagonist ingredients. Examples of such transmucosal and transdermal vehicles may be found throughout the pharmaceutical literature, including in *Remington's Pharmaceutical Sciences*, 17th edition (1985).

The invention also comprehends methods of providing treatment for hyperaldosteronism and its sequelae to a patient in need of such treatment, said methods consisting of the administration to the patient of one or more pharmaceutical dosage forms containing as active ingredients at least one of the compounds of formula I from one to four times daily. The preferred total daily dosage of compounds of formula I in accordance with the novel method of treatment is from about 25 to about 1000 mg.

The above-described method of treatment may also be used in the case of patients suffering from hypertension, hypokalemia and edema associated with sodium retention even where a diagnois of hyperaldosteronism has not been confirmed.

The Examples set forth below provide detailed illustrations of the compounds, pharmaceutical compositions and methods of the present invention. The Examples are not intended, however, to limit or restrict the scope of the invention in any way, and should not be construed as providing starting materials, reagents, conditions, reaction parameters or ingredients which must be utilized exclusively to practice the present invention.

EXAMPLE 1

21-Hydroxy-20-methylenepregn-4-ene-3-one

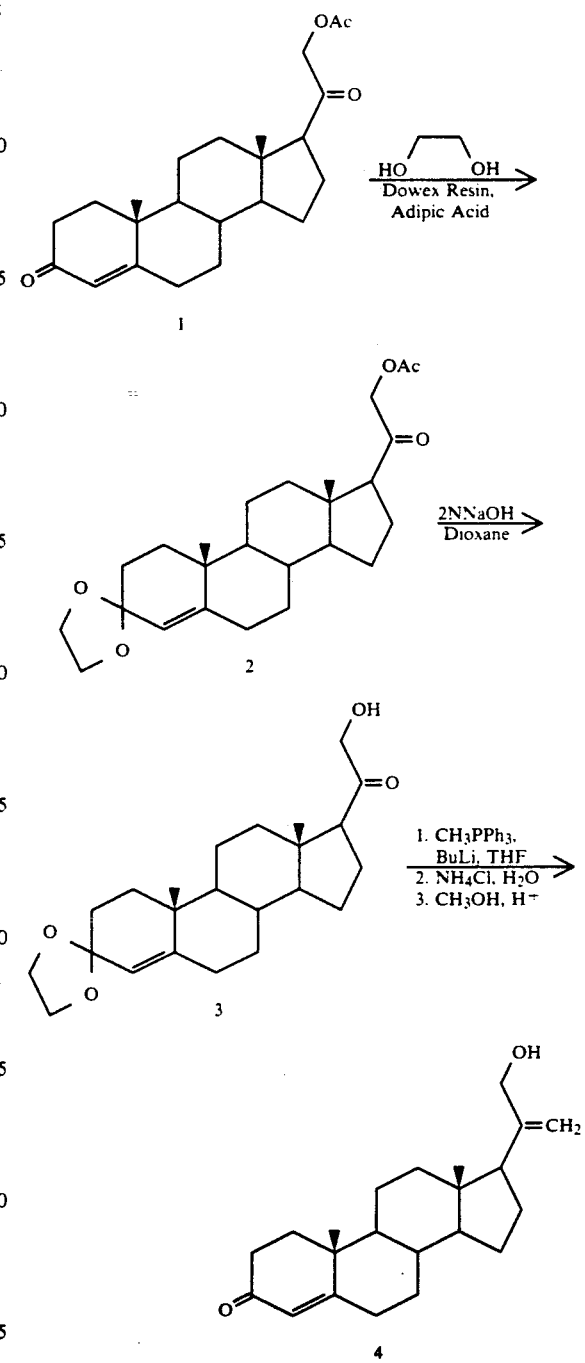

Desoxycorticosterone acetate-3-ketal, 2

A suspension of desoxycorticosterone acetate 1 (1.0 g, 2.68 mmole), adipic acid (0.20 g, 1.37 mmole) and Dowex 50X8-200 ion exchange resin (0.30 g) in anhydrous benzene (75 ml) was refluxed 18 hours with azeotropic removal of water. The reaction mixture was cooled, concentrated in vacuo and the residue dissolved in $CH_2Cl_2$ (100 ml). The organic phase was washed with $NaHCO_3$ (70 ml), $H_2O$ (70 ml) and saturated NaCl (70 ml), dried (anhy. $Na_2SO_4$) and concentrated in vacuo. The white semisolid obtained was triturated with hexanes, filtered and air dried to afford 2 (1.02 g, 91%). A portion was recrystallized from 10% EtOAc/Hexanes to give the final product as a white solid: m.p. 167°–169° C.; $M^{30}$, 416.

Desoxycorticosterone-3-ketal, 3

A solution of the acetate 2 (0.75 g, 1.80 mmole) in a 2N NaOH (3 ml)/Dioxane (9 ml) mixture was stirred 2 hours at room temperature. The basic solution was neutralized with Dowex 50X8-200 ion exchange resin, filtered and the filtrate concentrated in vacuo. The residue obtained was dissolved in $CH_2Cl_2$ (25 ml) containing MeOH (5 ml), the organic system washed with $H_2O$ (20 ml), and saturated NaCL (20 ml), dried (anhy. $Na_2SO_4$) and concentrated in vacuo to afford 3 (0.532 g, 80%) as a white foam. No further purification was attempted.

21-Hydroxy-20-methylenepregn-4-ene-3-one, 4 n-Buthyl lithium (5.10 ml, 10.20 mmole) was added slowly to a stirred suspension of methyl triphenylphosphonium bromide (3.69 g, 10.33 mmole) in anhydrous THF (35 ml). The resulting solution was stirred 30 minutes at room temperature, followed by the addition of 3 (0.763 g, 2.04 mmole) in THF (2ml). The reaction mixture was stirred 18 hours at room temperature, quenched with $NH_4Cl$ (2.0 g) in $H_2O$ (5 ml) and stirred 30 minutes at room temperature. The organic phase was separated, washed with saturated $NaHCO_3$ solution (70 ml), dried (anhy. $Na_2SO_4$) and concentrated in vacuo. Radial chromatography (50% EtOAc/Hexanes) of the residue afforded a yellow oil (0.55 g). The oil was dissolved in a $CH_3OH$ (10 ml)/6N HCl (2 ml) solution and refluxed 2 hours. The reaction mixture was cooled, neutralized with $NH_4OH$ and concentrated in vacuo. Preparative chromatography (30% EtOAc/Hexanes) afforded 4 (0.19 g, 28%) as a pale yellow waxy solid. $M^-$, 328.

EXAMPLE 2

21-Hydroxy-20-difluoromethylenepregn-4-ene-3-one

The procedure of Example 1 was followed, but a warm solution of $ClF_2CO_2Na$ in N-methylpyrrolidone was added dropwise to a hot solution of the ketal 3 and $Ph_3P$ in N-methylpyrrolidone to yield the difluoromethylene analog of the product of Example 1.

In general, various compounds of formula I can be produced by following the procedure of Example 1 but substituting the Wittig reagent $Ph_3P=CR_1R_2$ (either as a starting reagent or generated in situ, as in Example 1), wherein $R_1$ and $R_2$ are the desired substituents, for the reagent $Ph_3P=CH_2$ used in Example 1.

EXAMPLE 3

In Vitro Assay

The activity of the compound of Example 1 in inhibiting aldosterone synthesis from DOC was assayed in vitro. Beef glomerulosa was digested with collagenase and 600,000 of the cells were added to each of five reaction tubes, labeled 0–4. Each tube contained cold DOC as a substrate.

ACTH ($10^{-7}$ moles) was added to each tube. The compound of example 1 was then added to tubes 1–4, but not to tube 0 (control). The concentrations of the test compound added to tubes 1–4 were $10^{-6}$, $10^{-7}$, $10^{-8}$ and $10^{-9}$ moles, respectively. All tubes were incubated at 37° C. for two hours in a metabolic incubator under an atmosphere of 95% oxygen. After incubation, each tube was assayed for corticosterone (CS), 18-hydroxy-corticosterone, 18-hydroxy-DOC and aldosterone. The rates of synthesis of each of these four compounds, expressed in pM/hr./ml, are set forth in Table 1.

TABLE 1

| Tube | CS | 18-hydroxy-CS | 18-hydroxy DOC | Aldosterone |
|---|---|---|---|---|
| 0 | 846.9 | 323.2 | 96.3 | 319.6 |
| 1 | 1212.6 | 197.3 | 30.4 | 73.3 |
| 2 | 1044.7 | 188.2 | 42.8 | 94.7 |
| 3 | 1175.5 | 220.2 | 35.3 | 85.9 |
| 4 | 919.0 | 247.1 | 27.5 | 76.2 |

EXAMPLE 4

Pharmaceutical Composition 5.0 mg of the compound of Example 1 is admixed with carboxymethylcellulose, corn starch and sucrose. The resultant mixture is compressed into a tablet suitable for oral administration.

EXAMPLE 5

Method of Treatment

A patient requiring treatment for primary aldosteronism is administered a tablet prepared in accordance with Example 5 from one to four times daily.

It has thus been shown that there are provided compounds, compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

We claim:

1. A compound having the structural formula:

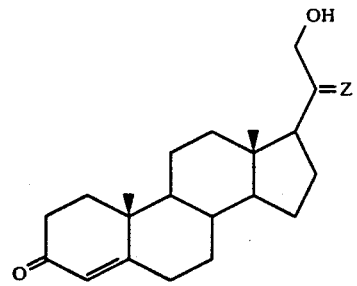

wherein Z is S, $CR_1R_2$ or $NR_5$, and wherein $R_1$ and $R_2$ are each independently selected from the group consisting of hydrogen, halogen, $C_1$–$C_5$ alkyl, $C_1$–$C_5$ alkenyl, aryl, aralkyl, and —$(CH_2)_nYR_3$, —$(CH_2)_nNR_3R_4$ or —$(CH_2)_nCO_2R_3$ wherein n is an integer from 0 to 4, $R_3$ and $R_4$ are $C_1$–$C_4$ alkyl or alkenyl, aryl or aralkyl and Y is oxygen or sulfur, and $R_5$ is selected from the group consisting of $H_2NCONH$, $H_2NCSNH$, $ARH_2N$, $C_1$–$C_5$ alkyl or alkyoxy, aryl and aryloxy.

2. A compound according to claim 1 wherein Z is $CR_1R_2$ and at least one of $R_1,R_2$ is hydrogen.

3. A compound according to claim 1 wherein Z is $CR_1R_2$ and at least one of $R_1,R_2$ is halogen.

4. A compound according to claim 3 wherein at least one of $R_1,R_2$ is fluoro.

5. 21-hydroxy-20-methylenepregn-4-ene-3-one.

6. 21-hydroxy-20-difluoromethylenepregn-4-ene-3-one.

7. A pharmaceutical composition comprising from about 5.0 to about 100 mg of a compound according to claim 1 and an inert, pharmaceutically-acceptable excipient or vehicle.

8. A composition according to claim 7 suitable for oral administration.

9. A composition according to claim 8 in the form of a tablet, capsule, caplet, pill, lozenge or liquid.

10. A composition according to claim 9 in the form of a tablet.

11. A composition according to claim 7 suitable for parenteral administration.

12. A composition according to claim 7 suitable for transmucosal or transdermal administration.

13. A method of treating a patient suffering from hyperaldosteronism, hypertension, hypokalemia or edema associated with sodium retention, consisting of the administration to said patient of a pharmaceutical composition according to claim 7 from one to four times daily.

* * * * *